US010799852B2

(12) United States Patent
Nubel et al.

(10) Patent No.: US 10,799,852 B2
(45) Date of Patent: Oct. 13, 2020

(54) CATALYST FOR ETHYLBENZENE CONVERSION IN A XYLENE ISOMERIZATION PROCESS

(71) Applicant: BP Corporation North America Inc., Houston, TX (US)

(72) Inventors: Philip Nubel, Naperville, IL (US); Jeffrey Amelse, Batavia, IL (US)

(73) Assignee: BP Corporation North America Inc., Houston, TX (US)

( * ) Notice: Subject to any disclaimer, the term of this patent is extended or adjusted under 35 U.S.C. 154(b) by 0 days.

(21) Appl. No.: 15/771,529

(22) PCT Filed: Oct. 27, 2016

(86) PCT No.: PCT/US2016/059115
§ 371 (c)(1),
(2) Date: Apr. 27, 2018

(87) PCT Pub. No.: WO2017/075214
PCT Pub. Date: May 4, 2017

(65) Prior Publication Data
US 2018/0345257 A1    Dec. 6, 2018

Related U.S. Application Data

(60) Provisional application No. 62/247,371, filed on Oct. 28, 2015.

(51) Int. Cl.
*B01J 29/48* (2006.01)
*B01J 29/40* (2006.01)
*C07C 5/27* (2006.01)
*B01J 21/08* (2006.01)
*B01J 35/00* (2006.01)

(52) U.S. Cl.
CPC .............. *B01J 29/48* (2013.01); *B01J 21/08* (2013.01); *B01J 29/40* (2013.01); *B01J 35/0006* (2013.01); *C07C 5/2708* (2013.01); *C07C 5/2737* (2013.01); *C07C 5/2775* (2013.01); *B01J 2229/42* (2013.01); *C07C 2529/40* (2013.01); *C07C 2529/48* (2013.01); *Y02P 20/52* (2015.11)

(58) Field of Classification Search
CPC ........ B01J 29/40; B01J 29/48; B01J 35/0006; B01J 21/08; B01J 2229/42; C07C 5/2708; C07C 5/2737; C07C 5/2775; C07C 2529/40; C07C 2529/48; Y02P 20/52
See application file for complete search history.

(56) References Cited

U.S. PATENT DOCUMENTS

| 4,163,028 | A | * | 7/1979 | Tabak ..................... B01J 29/44 585/481 |
| RE31,782 | E | | 12/1984 | Olson et al. |
| 4,908,342 | A | | 3/1990 | McWilliams et al. |
| 5,028,573 | A | | 7/1991 | Brown et al. |
| 5,516,956 | A | * | 5/1996 | Abichandani ............ B01J 29/44 585/475 |
| 6,518,472 | B1 | | 2/2003 | Feinstein et al. |
| 7,297,830 | B2 | | 11/2007 | Bogdan et al. |
| 8,058,496 | B2 | | 11/2011 | Bogdan et al. |
| 8,697,929 | B2 | | 4/2014 | Ou et al. |
| 8,889,940 | B2 | | 11/2014 | Bogdan et al. |
| 2006/0030478 | A1 | * | 2/2006 | Raich ..................... B01J 29/068 502/66 |

FOREIGN PATENT DOCUMENTS

| CN | 103288578 A | 9/2013 |
| CN | 104353487 A | 2/2015 |
| WO | WO 2014/150863 | 9/2014 |

OTHER PUBLICATIONS

"Information Disclosure," paper dated May 21, 2020.

* cited by examiner

*Primary Examiner* — In Suk C Bullock
*Assistant Examiner* — Jason Y Chong
(74) *Attorney, Agent, or Firm* — McDonnell Boehnen Hulbert & Berghoff LLP

(57) ABSTRACT

The present invention relates to a method for converting a feed mixture comprising an aromatic C8 mixture of xylenes and ethylbenzene in which the para-xylene content of the xylene portion of the feed is less than equilibrium to produce a product mixture of reduced ethylbenzene content and a greater amount of para-xylene, which method comprises contacting the feed mixture at conversion conditions with a first catalyst having activity for the conversion of ethylbenzene, and with a second catalyst having activity for the isomerization of a xylene.

10 Claims, No Drawings

CATALYST FOR ETHYLBENZENE CONVERSION IN A XYLENE ISOMERIZATION PROCESS

FIELD OF THE INVENTION

The present invention relates to a catalyst composition, its preparation, and its use in ethylbenzene dealkylation.

BACKGROUND OF THE INVENTION

Hydrocarbon mixtures containing $C_{8+}$ aromatics are by-products of certain oil refinery processes including, but not limited to, catalytic reforming processes. These hydrocarbon mixtures typically contain up to about 30 weight percent (wt. %) $C_{9+}$ aromatics, up to about 10 wt. % non-aromatics, up to about 50 wt. % ethylbenzene, the balance (e.g., up to about 100 wt. %) being a mixture of xylene isomers. Most commonly present among the $C_8$ aromatics are ethylbenzene ("EB"), and xylene isomers, including meta-xylene ("mX"), ortho-xylene ("oX"), and para-xylene ("pX"). Typically, when present among the $C_8$ aromatics, ethylbenzene is present in a concentration of up to about 20 wt. % based on the total weight of the $C_8$ aromatics. The three xylene isomers typically comprise the remainder of the $C_8$ aromatics, and are present at an equilibrium weight ratio of about 1:2:1 (oX:mX:pX).

The separation of xylene isomers has been of particular interest because of the usefulness of para-xylene in the manufacture of terephthalic acid which is used in the manufacture of polyester fabric. However, because the boiling points of ethylbenzene (EB), ortho-xylene (oX), meta-xylene (mX) and para-xylene (collectively referred to as "$C_8$ aromatics") are close, they are difficult to separate by fractional distillation. Ethylbenzene can be converted to other products, which can be removed from the $C_8$ aromatics by fractional distillation.

For example the para-xylene production unit may contain a catalyst reactor for pretreatment of a $C_8$ aromatic feed to reduce the amount of ethylbenzene in the feed by ethylbenzene conversion. The ethylbenzene may be selectively eliminated from the $C_8$ aromatics via dealkylation to provide benzene and ethane.

In ethylbenzene dealkylation it is a primary concern to ensure not just a high degree of conversion to benzene but also to avoid xylene loss. Xylenes may typically be lost due to transalkylation, e.g. between benzene and xylene to give toluene, or by addition of hydrogen to form, for example, alkenes or alkanes.

It is therefore the aim of the present invention to provide a catalyst that will convert ethylbenzene to benzene with a high selectivity without xylene loss.

SUMMARY OF THE INVENTION

The present invention relates to a catalyst system suitable for the isomerization of xylene and conversion of ethylbenzene in a feed containing xylene and ethylbenzene comprising a first catalyst having activity for the conversion of ethylbenzene, a second catalyst having activity for the isomerization of xylene.

The present invention also relates to a method for converting a feed mixture comprising an aromatic $C_8$ mixture of xylenes and ethylbenzene in which the para-xylene content of the xylene portion of the feed is less than equilibrium to produce a product mixture of reduced ethylbenzene content and a greater amount of para-xylene, which method comprises contacting the feed mixture at conversion conditions with a first catalyst having activity for the conversion of ethylbenzene, and with a second catalyst having activity for the isomerization of a xylene.

The present invention provides a two component catalyst system for isomerizing a feed containing an aromatic $C_8$ mixture of ethylbenzene and xylene in which the para-xylene is less than at thermal equilibrium which comprises a first catalyst having activity for the conversion of ethylbenzene, and a second catalyst having activity for the isomerization of a xylene.

The present invention includes a process for isomerizing a feed containing an aromatic $C_8$ mixture of ethylbenzene and xylene in which the para-xylene is less than at thermal equilibrium which comprises contacting the feed under isomerization conditions with a two component catalyst system including component (1) and component (2), wherein component (1) comprises a catalyst having activity for the conversion of ethylbenzene, and component (2) comprises a catalyst having activity for the isomerization of a xylene and wherein the component (2) is located in the system below component (1) relative to a flow of the ethylbenzene/xylene feed through the catalyst system.

Preferably, the first catalyst having activity for the conversion of ethylbenzene is, an acidic molecular sieve which is characterized by a constraint index in the approximate range of about 1 to about 12, more preferably it is a zeolite, preferably a crystalline aluminosilicate zeolite having a particle size of at least about 1 micron. In one embodiment of the invention, the EB conversion catalyst may contain a hydrogenation metal selected from metals of groups VI and VIII of the Periodic Table of Elements.

The second catalyst having activity for the isomerization of xylene is preferably, an acidic molecular sieve which is characterized by a constraint index in the approximate range of about 1 to about 12. Preferred molecular sieves are borosilicate molecular sieves or ZSM-type zeolite molecular sieves. The molecular sieve used is preferably dispersed on alumina, silica or another suitable matrix. In one embodiment of the invention, the xylene isomerization catalyst may contain a hydrogenation metal selected from metals of groups VI and VIII of the Periodic Table of Elements.

In one embodiment what is provided is a process for isomerizing a feed stream comprising xylenes and ethylbenzene, the process comprising:

contacting the feed stream with a first catalyst in a dual-bed catalyst system to produce a first effluent stream; and contacting the first effluent stream with a second catalyst in the dual-bed catalyst system to produce a second effluent stream, wherein the first catalyst comprises an aluminosilicate molecular sieve with up to 0.8 weight percent aluminum, wherein the first catalyst has activity for the conversion of ethylbenzene, wherein about 20 percent or more of the ethylbenzene in the feed stream is converted to hydrocarbons other than ethylbenzene, and wherein EBC/Xylene Loss is at least 45 when about 30 percent of the ethylbenzene is converted The aluminosilicate molecular sieve comprises about 0.7+/−0.05 weight percent aluminum. About 33 percent of the ethylbenzene in the feed stream is converted to hydrocarbons other than ethylbenzene. The aluminosilicate molecular sieve is on a support, wherein the support comprises silica. In one embodiment the support comprises at least 50% silica. In one embodiment the aluminosilicate molecular sieve is ZSM-5 aluminosilicate zeolite. In one embodiment, the second catalyst has activity for isomerization of xylenes.

In another embodiment, what is provided is a catalyst composition comprising an aluminosilicate molecular sieve with MFI framework with up to 0.8 weight percent aluminum, wherein the catalyst composition has activity for the conversion of ethylbenzene, and wherein crystals of the catalyst composition have average lengths in the range of about 5 to about 25 microns and average widths in the range of about 1 to about 10 microns and average thickness in the range of about 1 to about 10 microns.

In one embodiment, the aluminosilicate molecular sieve comprises about 0.5 to 0.8 wt % Al, more preferably 0.7+/−0.05 weight percent Al, and most preferably 0.7 wt % Al. In one embodiment, the crystals of the catalyst composition have average lengths between about 5 microns and 25 microns, and have average widths and thicknesses of between about 1 micron and 10 microns. In one embodiment, the aluminosilicate molecular sieve is on a support, wherein the support comprises silica. In one embodiment, the aluminosilicate molecular sieve is ZSM-5 aluminosilicate zeolite.

DETAILED DESCRIPTION OF THE INVENTION

The first catalyst component of the dual-bed catalyst system is a large-particle aluminosilicate molecular sieve with 0.5-0.8 wt % Al, more preferably 0.7+/−0.05 wt % Al, and most preferably 0.7 wt % Al content on a predominantly silica support. The first catalyst comprises about 10% to about 90%, and more preferably from about 40% to about 80% of the dual-bed catalyst system and is designed to hydrodeethylate ethylbenzene to ethane and benzene ahead of the second catalyst.

The present invention provides a novel means for stabilizing the xylene isomerization activity of a dual bed xylene isomerization catalyst system. This invention is useful for isomerizing a feed containing an aromatic $C_8$ mixture of xylenes and ethylbenzene (EB) in which the para xylene content of the xylene-containing portion of the feed is less than the equilibrium content, to produce a product stream of reduced ethylbenzene content and a greater amount of desired para xylene. Para-xylene is an important hydrocarbon feed material for the manufacture of terephthalic acid. In the present invention, a novel ethylbenzene conversion catalyst is provided having higher ethylbenzene conversion activity.

The ethylbenzene conversion catalyst is a catalyst that selectively catalyzes the conversion of ethylbenzene in the feed mixture to another compound or compounds that can easily be removed from the product mixture. For example, within the scope of the invention, ethylbenzene conversion can occur by a deethylation reaction, whereby the ethylbenzene is catalytically converted to benzene and a mixture of ethylene and ethane.

In processes for the manufacture of pure para-xylene, the para-xylene is separated from a $C_8$ feed mixture of xylenes and ethylbenzene using standard methods such as crystallization or adsorption. After removal of the para-xylene, the mother liquor or raffinate is recycled and subjected to isomerization to reestablish a near equilibrium mixture of xylenes. In this isomerization, process, meta-xylene and ortho-xylene are converted to para-xylene. However, it is very difficult to separate ethylbenzene from the xylenes prior to recycle using ordinary separation techniques.

If the ethylbenzene is not removed, it accumulates in the process stream to unacceptable levels. Rather than separate ethylbenzene, most processes for preparing pure para-xylene employ a means to convert ethylbenzene to compounds that can be removed by ordinary separation processes, such as, for example, distillation. The ethylbenzene conversion catalysts described herein serve to affect such conversion reactions.

The xylene isomerization catalyst is a catalyst that will catalyze the conversion of one xylene, such as meta-xylene or ortho-xylene, to another xylene, such as para-xylene. In particular, effective xylene isomerization catalysts will isomerize a mixture of xylenes where the xylenes are present in non-equilibrium amounts to a mixture containing, or very nearly containing, the xylenes in equilibrium amounts at the temperature used for the isomerization reaction. For example, a mixture of xylenes containing ortho-xylene, meta-xylene and para-xylene, where the para-xylene is present in less than the equilibrium amount, can be converted by an effective xylene isomerization catalyst to a mixture of xylenes where the ortho-, meta- and para-xylenes are present at or very near their equilibrium amounts.

This invention is a catalyst system suitable for the isomerization of a xylene and conversion of ethylbenzene in a feed containing xylene and ethylbenzene comprising a novel first catalyst having activity for the conversion of ethylbenzene, and a second catalyst having activity for the isomerization of a xylene where the second catalyst is located in the system below the first catalysts relative to a flow of feed mixture through the catalyst system.

This invention is also a method for converting a feed mixture comprising an aromatic $C_8$ mixture of xylenes and ethylbenzene in which the para-xylene content of the xylene portion of the feed is less than equilibrium to produce a product mixture of reduced ethylbenzene content and a greater amount of para-xylene, which method comprises contacting the feed mixture at conversion conditions with a first catalyst having activity for the conversion of ethylbenzene, and with a second catalyst having activity for the isomerization of a xylene, wherein the second catalyst is positioned below the first catalyst relative to the flow of the feed mixture through the catalysts.

Xylene isomerization feeds, processed in accordance with the invention are any aromatic $C_8$ mixture containing ethylbenzene and xylene(s). Generally, such a mixture will have an ethylbenzene content in the approximate range of about 5 to about 60 weight %, an ortho-xylene content in the approximate range of about 0 to about 35 weight %, a meta-xylene content in the approximate range of about 20 to about 95 weight %, and a para-xylene content in the approximate range of about 0 to about 15 weight %. The feed in addition to the above aromatic $C_8$ mixture can contain non-aromatic hydrocarbons, such as paraffins and naphthenes. The paraffins and naphthenes will generally comprise about 0 to about 20 weight % of the feed; generally, the paraffins and naphthenes will comprise $C_8$-$C_{10}$ paraffins and naphthenes.

The catalyst system used in accordance with the invention is multicomponent. The function of the first catalyst component is to effect conversion of ethylbenzene and $C_8$-$C_{10}$ paraffins and naphthenes to byproducts which are easily separated from the $C_8$ aromatics stream. The function of the second catalyst component is to effect isomerization of the xylene components in the feed to thermal equilibrium.

This invention can be used for, but is not limited to, vapor phase isomerization of a mixture of xylenes with a transalkylation-type (i.e., wherein EB is primarily converted via transalkylation to diethylbenzenes) dual bed catalyst for stabilizing the xylene isomerization activity of the xylene isomerization catalyst. The reaction conditions for the method of this invention are suitably a temperature of about 480° F. (248.8° C.) to about 1000° F. (537.8° C.), preferably about 500° F. (260° C.) to about 850° F. (454.4° C.), and more preferably about 600° F. (315.6° C.) to about 800° F. (426.7° C.); a pressure of about 0 to about 1000 psig, preferably about 50 to about 600 psig, more preferably about 100 to about 400 psig, and most preferably about 150 to about 300 psig; a hydrogen-to-total hydrocarbon mole ratio of from about 0.5:1 to about 10:1, preferably from about 1:1 to about 10:1, more preferably from about 1:1 to about 6:1, and most preferably from about 1:1 to about 3:1. The Weight Hourly Space Velocity (WHSV) may be in the range of from about 0.5 to about 100, preferably about 2 to about 50, more preferably about 3 to about 20, and most preferably about 4 to about 14. Hydrogen is typically included to hydrogenate coke precursors and hence minimize catalyst deactivation.

In the present invention, either or both of the EB conversion and xylene isomerization components may additionally contain a hydrogenation metal. Such hydrogenation metal may include, but is not limited to, one or more of molybdenum, platinum, palladium, rhodium, or ruthenium.

Even where the EB conversion catalyst component and/or the xylene isomerization catalyst component additionally contain a hydrogenation metal, it is expected that a hydrogenation bed, for example, a molybdenum on alumina catalyst, would still hydrogenate olefins not hydrogenated over the first catalyst bed, and therefore reduce the deactivation of the xylene isomerization component, thus extending its useable life. In general, the xylene isomerization reaction is carried out in a fixed bed flow reactor containing the catalyst system described above. In a preferred embodiment the feed is cascaded over the catalyst system disposed in the reactor in at least two sequential beds, i.e., the EB conversion catalyst bed, and then the xylene isomerization catalyst bed. The conversion process of the invention could also be carried out in separate sequential reactors wherein the feed would first be contacted with the EB conversion catalyst in a reactor and the resulting effluent stream would then be contacted with the xylene isomerization catalyst in a second reactor.

Catalyst components one and two (i.e., the EB conversion and xylene isomerization catalysts, respectively) contain an acidic molecular sieve which is characterized by a constraint index in the approximate range of about 1 to about 12. Molecular sieves having such a constraint index are often grouped as members of the class of molecular sieves referred to as shape selective. Although an MFI-type of molecular sieve was used in the EB conversion and xylene isomerization components of the dual bed catalyst system in the embodiment of this invention described in the Examples, other types of molecular sieve catalysts can also be used (e.g., ZSM-11, ZSM-12, ZSM-35, ZSM-38 and other similar materials).

The amount of catalysts and the relative amount of catalysts used in the catalyst system and process of this invention are the amounts that provide for the desired ethylbenzene conversion and xylene isomerization at the reaction conditions that are employed.

When a molecular sieve is used as a component of the isomerization or ethylbenzene conversion catalyst, the amount of molecular sieve can be about 1% to about 100% by weight, more preferably about 10 to about 70% by weight, with the remainder preferably being support matrix material such as alumina or silica. Preferably the support material is silica. The weight ratio of ethylbenzene conversion catalyst to isomerization catalyst is suitably about 1:1 to about 6:1. The weight ratio of ethylbenzene catalyst to hydrogenation catalyst is suitably about 1:1 to about 5:1.

Ethylbenzene conversion catalysts suitable for use in the present invention include but are not limited to Al-MFI molecular sieve dispersed on silica and large particle size molecular sieves, particularly a ZSM-5-type of molecular sieve having a particle size of at least about 1 micron, dispersed on silica, alumina, silica/alumina or other suitable support. The support material is preferably silica. Suitable catalysts based on a ZSM-type molecular sieve, for example, ZSM-5 molecular sieves, are described in U.S. Pat. No. Re. 31,782, which is incorporated herein by reference in its entirety.

In one embodiment what is provided is a process for isomerizing a feed stream comprising xylenes and ethylbenzene, the process comprising:

contacting the feed stream with a first catalyst in a dual-bed catalyst system to produce a first effluent stream; and contacting the first effluent stream with a second catalyst in the dual-bed catalyst system to produce a second effluent stream, wherein the first catalyst comprises an aluminosilicate molecular sieve with up to 0.8 weight percent aluminum, wherein the first catalyst has activity for the conversion of ethylbenzene, wherein about 20 percent or more of the ethylbenzene in the feed stream is converted to hydrocarbons other than ethylbenzene, and wherein EBC/Xylene Loss is at least 45 when about 30 percent of the ethylbenzene is converted.

The aluminosilicate molecular sieve comprises about 0.7+/−0.05 weight percent aluminum. About 33 percent of the ethylbenzene in the feed stream is converted to hydrocarbons other than ethylbenzene. The aluminosilicate molecular sieve is on a support, wherein the support comprises silica. In one embodiment the support comprises at least 50% silica. In one embodiment the aluminosilicate molecular sieve is ZSM-5 aluminosilicate zeolite. In one embodiment, the second catalyst has activity for isomerization of xylenes.

In another embodiment, what is provided is a catalyst composition comprising an aluminosilicate molecular sieve with MFI framework with up to 0.8 weight percent aluminum, wherein the catalyst composition has activity for the conversion of ethylbenzene, and wherein crystals of the catalyst composition have average lengths in the range of about 5 to about 25 microns and average widths in the range of about 1 to about 10 microns and average thickness in the range of about 1 to about 10 microns.

In one embodiment, the aluminosilicate molecular sieve comprises about 0.5 to 0.8 wt % Al, more preferably 0.7+/−0.05 weight percent Al, and most preferably 0.7 wt % Al. In one embodiment, the crystals of the catalyst composition have average lengths between about 5 microns and 25 microns, and have average widths and thicknesses of between about 1 micron and 10 microns. In one embodiment, the aluminosilicate molecular sieve is on a support, wherein the support comprises silica. In one embodiment, the aluminosilicate molecular sieve is ZSM-5 aluminosilicate zeolite.

The present invention will now be illustrated by the following Examples.

EXAMPLES

Example 1

Five small-scale ZSM-5 zeolite syntheses were performed using 125-cc Teflon-lined autoclave reactors. The following reagents were mixed at room temperature: 36-38 grams deionized water, 0.2-0.4 g sodium aluminum oxide (Alfa Aesar, 28.4 wt % Al), ethylenediamine (6.25 grams), tetrapropylammonium bromide (2.88 grams), and Nalco 2327 colloidal silica sol (27 grams). The amount of sodium aluminum oxide was varied (0.20 g, 0.30 g, 0.35 g, or 0.40 g) to obtain different aluminum levels in the ZSM-5 zeolite product (0.5 wt %, 0.75 wt %, 0.88 wt %, and 1.0 wt %, respectively). A small amount of aqueous sulfuric acid solution was added to each mixture to adjust pH to 11.2-11.4. The mixtures were then charged into an autoclave and heated with agitation by rotational tumbling inside an oven for 72 hours at 170° C. After cooling, solid products were collected by filtration, washed with deionized water, dried and calcined in air for 4 hours at 538° C. The calcined ZSM-5 products were characterized by ICP (inductively coupled plasma spectroscopy) for elemental composition and XRD (X-ray diffraction) for measuring % ZSM-5 crystallinity relative to a reference ZSM-5. Preparation and analytical data are given in Table I.

Ten ZSM-5 zeolites with varying aluminum content were prepared on a larger scale using 1-liter stainless steel autoclaves equipped with internal agitators. The procedure was the same as above using the same relative amounts of reagents but at approximately 10-fold larger scale. The ten zeolite preparations were identical except for the amount of sodium aluminum oxide employed which was varied to obtain different aluminum contents in the ZSM-5 products. The mixtures were charged into a 1-liter autoclave and heated with agitation for 72 hours at 170° C. After cooling, solid products were collected by filtration, washed with deionized water, dried and calcined in air for 4 hours at 510° C. Silica-supported catalysts containing molybdenum (Mo) were prepared from each calcined ZSM-5 using Cabot CAB-O-SIL® HS-5 fumed silica powder in a mass ratio of 60:40 ZSM-5/silica. ZSM-5 powder (30 g) was dry-mixed with fumed silica powder (20 g). Deionized water (65-85 g) was added and the mixture stirred to form an aqueous slurry, after which ammonium heptamolybdate tetrahydrate (2.15 g in 9 g deionized water) was added and mixed in. This slurry was dried at 165° C. and calcined at 510° C. for 4 hours. The calcined catalysts were ground and sieved to 18-40 mesh size for catalytic testing. Characterization data for the larger-scale ZSM-5 zeolite and catalysts are given in Table II. The ZSM-5 zeolites are numbered 1-10 and the Mo-ZSM-5/silica catalysts prepared from them are designated with a letter "C" after the respective ZSM-5 zeolite number.

Fixed-bed reactor pilot plant tests of the Mo-ZSM-5/silica catalysts were performed at initial conditions of 700° F., 220 psig, 1.7 mole $H_2$/HC mole ratio, and 15.9 $h^{-1}$ WHSV HC (hydrocarbon) feed rate. The HC feed contained 9 wt % ethylbenzene (EB), 10 wt % p-xylene (pX), 53 wt % m-xylene (mX), 25 wt % o-xylene (oX), 1 wt % toluene, 0.5 wt % benzene. The catalysts were tested at the above conditions for 1 day. If EB conversions were not ~30%, the HC and $H_2$ feed rates were adjusted to obtain EB conversions of ~30% (27-33%) and the tests were continued for 1-2 additional days. Results of these tests are given in Table III.

TABLE I

Small-Scale ZSM-5 Zeolite Preparation and Analytical Data

| ZSM-5 | Sodium Aluminum Oxide used in preparation (grams) | Targeted Al Content in ZSM-5 Product (wt %) | Actual Al in ZSM-5 Product by ICP (wt %) | Na in ZSM-5 Product by ICP (ppm) | XRD Crysallinity* (%) |
|---|---|---|---|---|---|
| A | 0.20 | 0.5 | 0.54 | 162 | 94 |
| B | 0.20 | 0.5 | 0.50 | 145 | 97 |
| D | 0.30 | 0.75 | 0.74 | 682 | 26 |
| E | 0.35 | 0.88 | 0.91 | 834 | 27 |
| F | 0.40 | 1.0 | 1.01 | 251 | 95 |

*XRD crystallinity relative to a reference ZSM-5 zeolite

TABLE II

Larger-Scale ZSM-5 Zeolite and Catalyst Analytical Data

| ZSM-5 or Mo-ZSM-5/Silica Catalyst | Al wt % | Na ppm | XRD Cryst* | Mo wt % |
|---|---|---|---|---|
| 1 | 0.61 | 485 | 102% | — |
| 1C | | 382 | 58% | 2.8 |
| 2 | 0.72 | 467 | 102% | — |
| 2C | | 363 | 58% | 2.7 |
| 3 | 0.69 | 433 | 100% | — |
| 3C | | 388 | 58% | 3.0 |
| 4 | 0.69 | 399 | 97% | — |
| 4C | | 363 | 56% | 3.0 |
| 5 | 0.69 | 301 | 101% | — |
| 5C | | 285 | 59% | 2.3 |
| 6 | 0.77 | 215 | 95% | — |
| 6C | | 203 | 57% | 2.5 |
| 7 | 0.82 | 244 | 84% | — |
| 7C | | 246 | 48% | 3.2 |
| 8 | 0.88 | 293 | 97% | — |
| 8C | | 268 | 53% | 3.0 |
| 9 | 0.85 | 230 | 97% | — |
| 9C | | 193 | 57% | 2.3 |
| 10 | 1.03 | 493 | 103% | — |
| 10C | | 405 | 59% | 2.8 |

*XRD crystallinity relative to a reference ZSM-5 zeolite

TABLE III

Mo-ZSM-5/silica Catalyst Pilot Plant Test Results

| Catalyst | Al wt % in ZSM-5 zeolite | Days on Stream | HC WHSV (1/h) | EB Conv. (EBC) (%) | Xylene Loss (%) | EBC/Xylene Loss Ratio |
|---|---|---|---|---|---|---|
| 1C | 0.61 | 0.7 | 15.9 | 29.9 | 0.47 | 64 |
|    |      | 1.7 | 15.9 | 29.9 | 0.47 | 64 |
| 2C | 0.72 | 0.7 | 15.9 | 30.4 | 0.44 | 68 |
|    |      | 2.4 | 18.0 | 27.2 | 0.37 | 73 |
|    |      | 3.4 | 18.0 | 27.6 | 0.37 | 75 |
| 2C (2nd test) | 0.72 | 0.6 | 15.9 | 30.6 | 0.48 | 64 |
|    |      | 1.6 | 18.5 | 28.2 | 0.41 | 68 |
|    |      | 2.6 | 18.5 | 28.4 | 0.41 | 70 |
|    |      | 3.6 | 18.5 | 28.4 | 0.42 | 68 |
| 3C | 0.69 | 0.7 | 20   | 30.4 | 0.43 | 71 |
|    |      | 1.7 | 19   | 30.3 | 0.38 | 80 |
|    |      | 2.7 | 20.6 | 28.3 | 0.30 | 95 |
| 4C | 0.69 | 0.7 | 15.9 | 32.7 | 0.59 | 55 |
|    |      | 1.7 | 18.9 | 28.2 | 0.44 | 65 |
|    |      | 2.7 | 19.0 | 28.6 | 0.43 | 66 |

TABLE III-continued

Mo-ZSM-5/silica Catalyst Pilot Plant Test Results

| Catalyst | Al wt % in ZSM-5 zeolite | Days on Stream | HC WHSV (1/h) | EB Conv. (EBC) (%) | Xylene Loss (%) | EBC/ Xylene Loss Ratio |
|---|---|---|---|---|---|---|
| 5C | 0.69 | 1.7 | 18 | 27.6 | 0.34 | 82 |
|  |  | 2.7 | 18 | 28.7 | 0.35 | 82 |
|  |  | 3.7 | 18.3 | 28.5 | 0.36 | 79 |
| 6C | 0.77 | 0.7 | 15.9 | 31.9 | 0.58 | 55 |
|  |  | 1.7 | 19 | 29.4 | 0.51 | 57 |
|  |  | 2.7 | 20.5 | 28.3 | 0.47 | 61 |
| 7C | 0.82 | 1.8 | 22.5 | 27.7 | 0.97 | 29 |
| 8C | 0.88 | 1.7 | 22.5 | 28.4 | 0.73 | 39 |
| 9C | 0.85 | 1.7 | 25.0 | 27.3 | 0.82 | 33 |
| 10C | 1.03 | 1.7 | 26.8 | 30.3 | 0.75 | 40 |
|  |  | 2.0 | 26.8 | 30.0 | 0.72 | 42 |

Conditions: fixed-bed reactor, 2-4 day runs, 700° F., 220 psig, 1.7 H$_2$/HC molar

What is claimed is:

1. A process for isomerizing a feed stream comprising xylenes and ethylbenzene, the process comprising:
    contacting the feed stream with a first catalyst in a dual-bed catalyst system to produce a first effluent stream; and
    contacting the first effluent stream with a second catalyst in the dual-bed catalyst system to produce a second effluent stream,
    wherein the first catalyst comprises an aluminosilicate molecular sieve having a constraint index within the range of 1 to 12 and comprising 0.7+/−0.05 weight percent aluminum,
    wherein the aluminosilicate molecular sieve is ZSM-5 aluminosilicate zeolite,
    wherein the first catalyst comprises a hydrogenation metal,
    wherein the first catalyst has activity for the conversion of ethylbenzene and the second catalyst has activity for isomerization of xylenes,
    wherein about 20 percent or more of the ethylbenzene in the feed stream is converted to hydrocarbons other than ethylbenzene, and
    wherein EBC/Xylene Loss in the first effluent stream is at least 45 when about 30 percent of the ethylbenzene is converted.

2. The process of claim 1, wherein about 33 percent of the ethylbenzene in the feed stream is converted to hydrocarbons other than ethylbenzene.

3. The process of claim 1, wherein the aluminosilicate molecular sieve is on a support.

4. The process of claim 3, wherein the support comprises silica.

5. The process of claim 3, wherein the support comprises at least 50% silica.

6. The process of claim 1, wherein the feed stream is contacted with the first catalyst at a temperature of 500° F. to 850° F.

7. The process of claim 1, wherein the feed stream is contacted with the first catalyst at a temperature of 600° F. to 800° F.

8. The process of claim 1, wherein crystals of the first catalyst have average lengths in the range of about 5 to about 25 microns, average widths in the range of about 1 to about 10 microns, and average thicknesses in the range of about 1 to about 10 microns.

9. The process of claim 1, wherein crystals of the first catalyst have average lengths between about 5 microns and 25 microns.

10. The process of claim 1, wherein crystals of the first catalyst have average widths and thicknesses of between about 1 micron and 10 microns.

* * * * *